(12) United States Patent
Nakamura et al.

(10) Patent No.: US 9,763,973 B2
(45) Date of Patent: Sep. 19, 2017

(54) AGENT FOR TREATING HTLV-I ASSOCIATED MYELOPATHY

(71) Applicants: NAGASAKI UNIVERSITY, Nagasaki-shi, Nagasaki (JP); ReqMed Company, Ltd., Machida-shi, Tokyo (JP)

(72) Inventors: Tatsufumi Nakamura, Nagasaki (JP); Tadashi Matsumoto, Machida (JP)

(73) Assignees: Nagasaki University, Nagasaki (JP); ReqMed Company, Ltd., Machida (JP)

( * ) Notice: Subject to any disclaimer, the term of this patent is extended or adjusted under 35 U.S.C. 154(b) by 24 days.

(21) Appl. No.: 14/351,242

(22) PCT Filed: Oct. 12, 2012

(86) PCT No.: PCT/JP2012/076400
§ 371 (c)(1),
(2) Date: Apr. 11, 2014

(87) PCT Pub. No.: WO2013/054866
PCT Pub. Date: Apr. 18, 2013

(65) Prior Publication Data
US 2014/0235572 A1 Aug. 21, 2014

(30) Foreign Application Priority Data

Oct. 13, 2011 (JP) .................. 2011-226209

(51) Int. Cl.
*A61K 31/737* (2006.01)
(52) U.S. Cl.
CPC .................. *A61K 31/737* (2013.01)
(58) Field of Classification Search
CPC .................................................. A61K 31/737
USPC ........................................................ 514/54
See application file for complete search history.

(56) References Cited

U.S. PATENT DOCUMENTS 5,668,116 A * 9/1997 Cullis-Hill ......... A61K 47/4823
514/54
2007/0243218 A1* 10/2007 Ellinghuysen ....... A61K 9/0019
424/400

OTHER PUBLICATIONS

Caskey et al, AIDS Res. Hum. Retroviruses, 2007, 23(3), 365-371.*
Oh et al, Neurol. Clin., 2008, 26(3), 1-14.*
Ghosh et al, Agents and Actions, Supplements, 1993, 39, 195-206.*
Nakamura et al, Shared Research Reports, 2009, pp. 26-30—English Translation.*
Sydow et al, Biomed. Biochim. Acta, 1987, 6, 527-530.*
Tajima, K., J. of Clinical and Experimental Medicine, 1993, 165, 23-29, English translation.*
Ida et al., *Antiviral Research*, 23: 143-159 (1994).
Matsuo et al., *The Lancet*, 2: 1109-1113 (1986).
Nagasato et al., *Journal of the Neurological Sciences*, 115: 161-168 (1993).
Nakagawa et al., *Journal of Neurovirology*, 2: 345-355 (1996).
Nakamura et al., "Role of Small GTPases Involved in cell-to-cell spread of HTLV-I in HAM/TSP and Fundamental Study Aiming at Development of Novel Treatment Method with Polysulfate," HTLV-I no Seitainai Kansen Kakudai Kijo no Kaimei to sono Seigyo ni yoru HAM Chiryoho no Kaihatsu ni Kansuru Kenkyu Heisei 20 Nendo Sokatsu Buntan Kenkyu Hokokusyo, *Health and Labour Sciences Research Grant (kokoro-no-kenkokagaku-kenkyujigyo) Shared Research Reports*, pp. 26-30 (2009).
Tajima, Kazuo, *Journal of Clinical and Experimental Medicine*, 165: 23-29 (1993).
Taylor et al., *Retrovirology*, 3: 63 (2006).
Japanese Patent Office, International Search Report in International Patent Application No. PCT/JP2012/076400 (Dec. 11, 2012).
Nakamura et al., *Central Nervous System Agents in Medicinal Chemistry*, 9(2): 137-149 (2009).
Sydow et al., *Biomedica Biochimica Acta*, 46(6): 527-530 (1987).
European Patent Office, Supplementary European Search Report in European Patent Application No. 12840392 (Mar. 9, 2015).

* cited by examiner

*Primary Examiner* — Ganapathy Krishnan
(74) *Attorney, Agent, or Firm* — Leydig, Voit & Mayer, Ltd.

(57) ABSTRACT

The present invention provides a or therapeutic agent for HAM, containing pentosan polysulfate or a pharmaceutically acceptable salt thereof as an active ingredient. The present invention also provides an agent for improving a HAM-associated movement disorder, containing pentosan polysulfate or a pharmaceutically acceptable salt thereof as an active ingredient.

10 Claims, 3 Drawing Sheets

AGENT FOR TREATING HTLV-I ASSOCIATED MYELOPATHY

CROSS-REFERENCE TO RELATED APPLICATIONS

This patent application is the U.S. national phase of International Patent Application No. PCT/JP2012/076400, filed Oct. 12, 2012, which claims the benefit of Japanese Patent Application No. 2011-226209, filed on Oct. 13, 2011, which are incorporated by reference in their entireties herein.

TECHNICAL FIELD

The present invention relates to a prophylactic or therapeutic agent for HTLV-I-associated myelopathy (HAM). The present invention also relates to an improving agent for HAM-associated movement disorders.

BACKGROUND ART

Human T-cell lymphotropic virus (HTLV-I)-associated myelopathy (hereinafter to be also referred to as "HAM") is a chronically progressive myelitis induced by infection with HTLV-I, a human retrovirus. Although this disease is not a fatal disease, once it is developed, progressive gait disorders (finally in a bedridden state), dysuria and the like are certainly induced, and ADL and QOL of patients in the daily life are markedly limited. Therefore, this disease was designated as an intractable neurologic disease by the Ministry of Health, Labour and Welfare in 2008, and an urgent establishment of the treatment method therefor is highly demanded.

As a main, conventional treatment method for HAM is an immunomodulatory therapy such as administration of adrenal cortex hormone or interferon-α. This is a symptomatic therapy targeting chronic myelitis caused by HAM, which aims to improve clinical symptoms by the effect of a medicament having an immunomodulatory action. However, the effect of such treatment is not satisfactory, and the treatment takes a long time. Therefore, various problems including emergence of side effects, medical cost problem and the like have been pointed out (non-patent document 1). While alleviation of the above-mentioned problems has been tried by controlling the dose and dosing period of adrenal cortex, hormone and interferon-α, additional administration of vitamin C and the like, and the like, the problems have not been solved as yet. As other immunomodulatory therapy, various attempts such as plasma exchange therapy (non-patent document 2) and the like have been made. However, they also have similar problems.

As an anti-HTLV-I therapy for HAM, a zidovudine+lamivudine therapy has been reported. In a recent case-control study, the effectiveness thereof was not verified (non-patent document 3). In addition, an anti-HTLV-I therapy with an HDAC inhibitor valproic acid has a large problem in that it transiently and markedly increases the amount of peripheral blood HTLV-I provirus, which is a maximum risk factor for the HAM pathology.

The formation of HAM pathology starts with the infiltration of HTLV-I infected cells, which have increased markedly in the peripheral blood, into the spinal cord. Therefore, removal of the HTLV-I infected cells themselves from the body is considered to be the causal therapy of the disease; however, the treatment method has not been established yet.

The manner of HTLV-I infection is not infection with free virus particles but enlargement of infection by cell-to-cell spread. Specifically, HTLV-I starts cell-to-cell spread by the binding of coat protein gp46 of HTLV-I to HSPG (Heparan sulfate proteoglycan), which is a receptor of the target cell. Therefore, one target of the causal therapy is to prevent the binding and inhibit the cell-to-cell spread of HTLV-I, thereby preventing spread of HTLV-I in the body.

In relation thereto, one of the present inventors and others have reported that heparin, which is one of polysaccharide sulfates, shows an HTLV-I infection inhibitory action in a vitro test, and is clinically effective for HAM patients in an in vivo test (non-patent documents 4 and 5). However, heparin therapy has not been practicalized since consecutive and daily intravenous administration by injection is necessary, and a safety problem exists since heparin has a strong anticoagulant action.

As mentioned above, a causal therapy of HAM that can be practicalized has not been found to date. Moreover, various medicaments used for conventional HAM treatments failed to show an improving effect particularly as regards movement disorders associated with HAM, which has posed a large problem on medical treatments.

DOCUMENT LIST

Non-patent Documents non-patent document 1: Nakagawa M. et al., J. Neurovirol., vol. 2, p. 345-55 (1996)
non-patent document 2: Matsuo H. et al., Lancet, vol. 2, p. 1109-13 (1986)
non-patent document 3: Graham P. Taylor et al., Retrovirology, vol. 3: 63 (2006)
non-patent document 4: Nagasato K. et al., J. Neural. Sci., vol. 115, p. 161-8 (1993)
non-patent document 5: Ida H. et al., Antiviral Research, vol. 25 23, p. 143-59 (1994)
non-patent document 6: Tatsufumi Nakamura et al., The role of small GTPases involved in cell-to-cell spread of HTLV-I in HAM/TSP and fundamental study aiming at development of novel treatment method with polysulfate, kokoro-no-kenkokagaku-kenkyujigyo, Study relating to elucidation of mechanism of spread of HTLV-I infection within the body and development of HAM treatment method by control thereof, year 2008 summary and shared research reports (2009) p. 26-30

SUMMARY OF THE INVENTION

Problems to be Solved by the Invention

The present invention has been made in view of the above-mentioned current situation in the technical field. That is, the present invention aims to provide a prophylactic or therapeutic agent for HAM, which is useful for the basic prophylaxis or treatment of HAM, has high safety and can be practicalized rapidly. The present invention also aims to provide an agent for improving a HAM-associated movement disorder.

Means of Solving the Problems

The present inventors have conducted intensive studies in an attempt to solve the above-mentioned problems.

The present inventors first took note of the mechanism of preventing the binding of coat protein gp46 of HTLV-I and receptor HSPG of the target cell and inhibiting the cell-to-cell spread of HTLV-I, and performed intensive studies. As a result, they have confirmed in experiments in vitro that pentosan polysulfate, which is one of polysaccharide sulfates, has a very strong HTLV-I infection inhibitory action at a low dose as compared to heparin (the above-mentioned non-patent document 6). Pentosan polysulfate has already been sold for not less than 50 years as an antithrombotic and antihyperlipidemic drug mainly in Europe, and sold for the application aiming at mitigation of the pain and uncomfortable feeling due to interstitial cystitis in the US and Canada, and is a medicament with established safety. Also in Japan, clinical studies for osteoarthritis patients (Kumagai K. et al., BMC Clinical Pharmacology, vol. 10: 7 (2010)), and Phase 1 clinical studies targeting Japanese healthy male adults have already been performed, and the safety for Japanese people has also been confirmed. Therefrom pentosan polysulfate was expected to be a novel, safe and effective prophylactic or therapeutic drug as a causal therapy for HAM. Therefore, the present inventors have further studied the clinical effect of pentosan polysulfate in HAM patients. As a result, they have observed a decreasing tendency in the amount of HTLV-I provirus in the peripheral blood of HAM patients who underwent a pentosan polysulfate treatment. Furthermore, clinical effects of improved spasticity in the lower legs and shortened gait time were significantly observed in HAM patients by a pentosan polysulfate treatment. As a novel finding obtained at this time, the observed improvement effect on the movement disorder is not necessarily correlated to a decrease in the amount of HTLV-I provirus, and suggests a possibility of a new action mechanism.

The present inventors have further conducted studies based on such findings and completed the present invention.

Accordingly, the present invention provides the following.

[1] A prophylactic or therapeutic agent for HTLV-I-associated myelopathy, comprising pentosan polysulfate or a pharmaceutically acceptable salt thereof as an active ingredient.
[2] The agent of the above-mentioned [1], wherein pentosan polysulfate or a pharmaceutically acceptable salt thereof is sodium pentosan polysulfate.
[3] An agent for improving a movement disorder of a lower leg relating to HTLV-I-associated myelopathy, comprising pentosan polysulfate or a pharmaceutically acceptable salt thereof as an active ingredient.
[4] The agent of the above-mentioned [3], wherein the movement disorder is spasticity or a gait disorder due to spastic paraplegia.
[5] The agent of the above-mentioned [4], wherein the movement disorder is a gait disorder due to spastic paraplegia.

Effect of the Invention

Since the medicament of the present invention can decrease HTLV-I infected cells at the end of the life of the infected cells by preventing spread of HTLV-I infected cells in the body of a subject, it can be used for a causal therapy of HAM. Apart from the effect of decreasing HTLV-I infected cells, it can improve or prevent progression of the clinical symptoms of HAM, particularly lower leg movement disorder. Various medicaments used heretofore for the treatment of HAM failed to show an improvement effect based on a medicinal action unlike the compound used in the present invention, and therefore, the compound can be the first medicament that can improve or prevent progression of the clinical symptoms of HAM. Since the medicament of the present invention expresses the effect at a low dose, it is highly safe and provides effects at a low administration frequency such as once a week and the like. Therefore, the medicament places only a small burden on HAM patients, is superior in the improvement of QOL, and can reduce an economical burden on patients. Furthermore, since pentosan polysulfate is already commercially available as a pharmaceutical product for other applications, the medicament of the present invention can be expected for early practicalization.

Moreover, since the improvement effect on the lower leg movement disorder by the medicament of the present invention is based on a different mechanism from that of a decrease in the amount of HTLV-I provirus, the medicament of the present invention may also be usable for the improvement of a lower leg movement disorder caused by an etiology other than HAM.

DESCRIPTION OF EMBODIMENTS

The contents of the present invention are explained in detail in the following. In the following, the above-mentioned prophylactic or therapeutic agent for HAM is referred to as the prophylactic or therapeutic agent of the present invention, and the above-mentioned improving agent for a lower leg movement disorder relating to HAM is referred to as the improving agent of the present invention. In addition, they are generically referred to the medicament of the present invention.

As mentioned above, the medicament of the present invention has an effect of preventing or treating HAM since it prevents an increase of HTLV-I in the body of the subject, thus decreasing HTLV-I infected cells. On the other hand, it also has an improving effect on the symptoms relating to HAM in the subject, besides the virus amount decreasing effect. Namely, the difference between the above-mentioned prophylactic or therapeutic agent and the improving agent mainly takes note of the object and effect of the administration of the medicament of the present invention, and they are not necessarily different as substances.

The medicament of the present invention contains pentosan polysulfate or a pharmaceutically acceptable salt thereof as an active ingredient.

The pentosan polysulfate contained in the medicament of the present invention as an active ingredient is polysaccharide sulfate extracted from a plant and semi-synthesized, and is structurally similar to heparan sulfate, which is polysaccharide present on almost all the cell surfaces and extracellular matrices in animals. In addition, sodium pentosan polysulfate, which is supplied in the world by bene pharmaChem GmbH & Co., KG (Munich, Germany) as a pharmaceutical product, can also be preferably used as the agent. The structure of sodium pentosan polysulfate is shown below.

The molecular weight of the pentosan polysulfate to be used for the medicament of the present invention is not particularly limited as long as it is suitable for administration to a subject for the purpose of preventing/treating or improving the symptoms of HAM, and varies depending on the production method thereof. It is generally about 4000 Da-about 6000 Da.

The pentosan polysulfate contained in the medicament of the present invention as an active ingredient may be used in the form of a neutral molecule or a pharmaceutically acceptable salt thereof, and the aforementioned salt can be a base addition salt. The base forming the aforementioned base addition salt may be an inorganic base or an organic base. While the inorganic base is not particularly limited, for example, ammonium hydroxide, alkali metal hydroxide, alkaline earth metal hydroxide, carbonate, hydrogen carbonate and the like can be mentioned. More specifically, for example, sodium hydroxide, potassium hydroxide, potassium carbonate, sodium carbonate, sodium hydrogen carbonate, potassium hydrogen carbonate, calcium hydroxide, calcium carbonate and the like can be mentioned. Also, while the organic base is not particularly limited, for example, ethanolamine, triethylamine, tris(hydroxymethyl) aminomethane and the like can be mentioned. As mentioned above, a preferable example thereof is, but is not limited to, sodium pentosan polysulfate, which is a salt of pentosan polysulfate and sodium hydroxide. These salts can be produced by a method known per se.

As mentioned above, pentosan polysulfate is a medicament that has already been sold abroad for 50 years or longer, and the safety has been established. In Japan, moreover, clinical studies in osteoarthritis patients, and Phase 1 clinical test for Japanese healthy male adults have already been performed, and the safety for Japanese people has also been confirmed. Thus, the medicament of the present invention can be used safely.

The medicament of the present invention can be used for the prophylaxis/treatment of HTLV-I-associated myelopathy or improvement of the symptoms by administration to mammals (e.g., human, monkey, horse, bovine, dog, mouse etc.), preferably human. It is said that there are 10 million to 20 million HTLV-I carriers in the world, and the medicament of the present invention can prevent HAM in, for example, HTLV-I carriers who have not developed HAM. In addition, the medicament of the present invention can treat HAM or improve symptoms thereof in, for example, patients diagnosed to have HAM by a comprehensive evaluation based on the clinical symptoms, test data and the like relating to HAM. In the present specification, the improvement of symptoms encompasses not only full or partial resolution of the symptoms but also prevention, reduction or delay of the degradation of the symptoms.

The symptoms relating to HTLV-I-associated myelopathy (HAM), which is the target for the improving agent of the present invention, are not particularly limited as long as they are symptoms emerged in patients in relation to the onset of HAM. Specific examples of the symptom include chronic inflammation of the spinal cord; movement disorder in various body parts (e.g., lower leg, hand, finger etc.); sensory disorders such as sense of numbness, pain and the like; bladder and rectal disturbances including urination difficulty, frequent urination and constipation; sweating disorder of the lower body; orthostatic hypotension; impotence; mild dementia and the like. These symptoms can be related to each other, and are not particularly limited. Effective target symptom for the improving agent of the present invention is HAM-related movement disorder in the lower leg. Examples of the movement disorder in the lower leg, which is related to HAM, include gait disorder and the like due to spasticity, spastic paraplegia of the lower leg. These are the particularly effective target symptoms for the improving agent of the present invention.

Spasticity is one type of hypertonia, and caused by an abnormal increase in the muscle stretch reflex. Clinically, spasticity is a speed-dependent resistance to stretch, which is defined to be the state wherein the muscle is excessively contracted due to the lack of suppression from the central nervous system, which finally leads to an increase in the reflection. As a measurement method of spasticity, the Ashworth scale is well known, and its modified version by Bohannon is often used clinically (modified Ashworth scale; Bohannon R W, Smith M B: Interrater reliability of a Modified Ashworth Scale of Muscle Spasticity. Phys Ther 67: 206-207, 1987). This is an index for the evaluation of spasticity in the following 6 stages.

0—No increase in muscle tone
1—Slight increase in muscle tone, manifested by a catch and release or minimal resistance at the end of the ROM when the affected part(s) is moved in flexion or extension
1+—Slight increase in muscle tone, manifested by a catch, followed by minimal resistance throughout the remainder (less than half) of the ROM
2—More marked increase in muscle tone through most of the ROM, but affected part(s) easily moved
3—Considerable increase in muscle tone, passive movement difficult
4—Affected part(s) rigid in flexion or extension.

The improving agent of the present invention, which is administered to patients with HAM-related spasticity of the lower leg, can provide, for example, improvement in one or more stages of the above-mentioned modified Ashworth scale, or a significant improvement admitted by an appropriate clinician, even though the stage does not change, or can prevent, reduce or delay aggravation in one or more stages, or a significant aggravation admitted by an appropriate clinician, even though the stage does not change.

As regards the gait disorder due to HAM-related spastic paraplegia, the gait disorder in the present specification includes not only disorder in walking but also disorder in running and ascending and descending stairs, as well as wheelchair state and bedridden state due to gait function disorders. As an index of gait disorder, the following motility dysfunction scales have been proposed (Osame M. et al., HTLV-I-associated myelopathy (HAM) revisited. HTLV-I and the Nervous System, Alan R. Liss, Inc, p. 213-223, 1989.):

0: No abnormality in walking or running
1: Slow running speed
2: Abnormality in walking (stumbling, stiffness of knees)
3: Unable to canter
4: Handrail needed for ascending or descending stairs
5: Walking while holding on to something with one hand
6: Unable to walk while holding on to something with one hand, but able to walk 10 m or more with both hands
7: Able to walk 5 m or more but not more than 10 m while holding on to something with both hands
8: Able to walk not more than 5 m while holding on to something with both hands
9: Unable to walk while holding on to something with both hands, but able to move on all fours
10: Unable to move on all fours, but able to move with knees, hip or the like on the floor
11: Unable to move by oneself, but able to roll over 12: Unable to roll over
13: Unable to move even a toe The improving agent of the present invention, which is administered to patients with gait disorder due to HAM-related spastic paraplegia, can provide, for example, improvement in one or more stages of the above-mentioned motility dysfunction scales, or a significant improvement admitted by an appropriate clinician, even though the stage does not change, or can prevent, reduce or delay aggravation in one or more stages, or a significant aggravation admitted by an appropriate clinician, even though the stage does not change.

The medicament of the present invention can take various dosage forms. Examples of the dosage form include oral preparations (e.g., capsule, tablet, granule, powder etc.), parenteral preparations (e.g., injection etc.) and the like.

For example, an oral preparation can be produced by a method known per se, including adding, for example, excipient (e.g., lactose, sucrose, starch etc.), disintegrant (e.g., starch, calcium carbonate etc.), binder (e.g., starch, gum arabic, carboxymethylcellulose, polyvinylpyrrolidone, hydroxypropylcellulose etc.), lubricant (e.g., talc, magnesium stearate, polyethylene glycol 6000 etc.) and the like to the above-mentioned pentosan polysulfate or a pharmaceutically acceptable salt thereof, compression molding the mixture, and then, where necessary, masking the taste or applying, by a method known per se, an enteric coating or a coating for sustained release. As a coating agent therefor, for example, general coating agents for forming film (e.g., hydroxypropylmethylcellulose, ethylcellulose, hydroxymethylcellulose, hydroxypropylcellulose, polyoxyethyleneglycol etc.), Tween 80, pluronic F68, enteric coating agents (e.g., cellulose acetate phthalate, hydroxypropylmethylcellulose phthalate, hydroxymethylcellulose acetate succinate, hydroxypropylmethylcellulose acetate succinate, methylmethacrylate-methacrylic acid copolymer, methylacrylate-methacrylic acid copolymer etc.), dyes (e.g., titanium oxide, ferric oxide red, talc) and the like can be used. For enteric coating, it is also effective to provide, by a method known per se, one or more intermediate layers composed of the above-mentioned coating agents for forming film between the central core containing the active ingredient and the enteric film.

In addition, the medicament of the present invention is also effective as an injection for parenteral administration. Examples of the injection include aqueous or nonaqueous isotonic aseptic injections, which may contain antioxidant, buffer, bacteriostatic agent, isotonic agent and the like. Moreover, aqueous or nonaqueous aseptic suspensions can be mentioned, which may contain suspending agent, solubilizer, thickener, stabilizer, preservative and the like. The preparation can be sealed in a container by a unit dose or several doses such as ampoule and vial. Since the medicament of the present invention can provide a high effect even without consecutive daily administration, even administration by injection can be preferably performed without markedly impairing the QOL of patients.

The dose, administration interval and the like of the medicament of the present invention are not particularly limited, and they can be appropriately selected according to the object. They can be determined by those of ordinary skill in the art and in consideration of various factors including the age, affected period, body weight, sex, disease state of patients, administration route, level of metabolism and excretion functions of patient, dosage form to be used, and the active ingredient to be administered. Specifically, for example, the medicament of the present invention is administered to an adult (body weight 50 kg) at a dose of the active ingredient of about 10 mg—about 200 mg at an administration interval of once in 1 to 7 days, preferably a dose of about 25 mg—about 150 mg at an administration interval of once in 2 to 7 days, particularly preferably at a dose of about 50 mg—about 100 mg at an administration interval of once in 3 to 7 days. As the virus amount decreases and the clinical symptoms improve in the subject due to the administration, the amount and frequency of the administration can be decreased.

The medicament of the present invention can be used in combination with other medicaments. Examples of such medicament include prednisolone, adrenal cortex hormone, interferon-α, vitamin C and the like, which have been conventionally administered for a symptomatic therapy of HTLV-I-associated myelopathy. As the effect of the medicament of the present invention is increasingly obtained, reduction of the dose or discontinuation of the medicament associated with the problem of side effects is possible.

EXAMPLES

The present invention is explained in more detail in the following by referring to Examples which are not to be construed as limitative.

1. Clinical Test of Treatment of HTLV-I-Associated Myelopathy (HAM) Patients with Pentosan Polysulfate

[Research Purpose]

Clinical tests were performed to confirm effectiveness and safety of subcutaneous injection of pentosan polysulfate to HAM patients. The following two points were the main objects.

(1) Verification of treatment effect from the aspects of lower leg motility function and urination function One of the present inventors and others confirmed in a test in vitro that pentosan polysulfate has a strong HTLV-I infection inhibitory action at a lower concentration compared to heparin. However, a test for clearly confirming the correlation between the strength of the HTLV-I infection inhibitory action and the clinical effect of pentosan polysulfate in HAM patients has not been performed to date.

The main symptoms of HAM are motility/gait disorders and the like. As items for the clinical evaluation of these symptoms, lower leg motility function (walking time, time for descending stairs, spasticity, motility dysfunction level etc.) tests and the like can be mentioned. By evaluating these items before and after administration of pentosan polysulfate, the treatment effect of subcutaneous injection of pentosan polysulfate on HAM was verified.

As the administration method, subcutaneous injection was used, which can inject pentosan polysulfate sufficiently into the body. In addition, the administration method was determined by reference to the dose and dosing period, which had been confirmed to be safe for Japanese people in clinical studies of pentosan polysulfate for osteoarthritis.

(2) Verification of treatment effect from the aspect of virus (HTLV-I) amount

In the peripheral blood of HAM patients, a marked increase in the amount of HTLV-I provirus is seen, and the removal of the virus from the body is expected to lead to the causal therapy. However, since a test for clearly confirming the correlation between the amount of virus and the clinical symptom has not been performed, the correlation between the level of decrease in the virus amount and the clinical effect is unknown.

Therefore, for virological evaluation, the amount of peripheral blood HTLV-I provirus was monitored, immunological markers predicted to vary depending on a decrease in the provirus was simultaneously monitored, and the effect of pentosan polysulfate on HTLV-I was verified. In addition, the clinical effects (lower leg motility function etc.) were evaluated simultaneously with the measurement of the virus amount, and the correlation between a decrease in the virus amount and the clinical effect was confirmed. Furthermore, the amount of HTLV-I provirus was measured before and after administration of pentosan polysulfate, and a virus, amount decreasing effect of pentosan polysulfate was confirmed, whereby the possibility of providing a causal therapy was verified.

[Method]

Test location: Nagasaki University Hospital

Subject: 12 cases of HAM patients (9 females, 3 males, age; 49-77 years old, duration of illness; 3-52 years) (Table 1).

Test method: Sodium pentosan polysulfate was subcutaneously administered by 25 mg for the first time (0 week), 50 mg 1 week later, 100 mg once a week from the second week to the 7th week to the brachial region. The test medicament was used in 1 ml ampoule of sodium pentosan polysulfate (100 mg/ml) supplied by bene pharmaChem of Germany.

Test items: the subjective symptoms and neurological observations (including spasticity, gait time, time for descending stairs, motility dysfunction level and the like) were checked at the time of screening, week 0 (initial administration), week 8 from the start of treatment (week 1 after completion of treatment) and week 12 from the start of treatment (week 5 after completion of treatment). Similarly, general clinical tests, and immunological (serum soluble IL-2 receptor (sIL-2R), peripheral blood lymphoblastogenesis test) and virological tests (amount of peripheral blood HTLV-I provirus (real-time quantitative PCR method), anti-HTLV-I antibody titer) were performed.

(Consideration for Ethical Aspect)

This clinical test was approved by the Nagasaki University Ethics Committee, and performed after obtaining written informed consent by sufficiently explaining the contents of the study.

TABLE 1 case list

| | gender | age | age of onset | duration of illness | movement disorder level |
|---|---|---|---|---|---|
| 1) | male | 57 | 6 | 51 | 6 |
| 2) | female | 62 | 34 | 28 | 10 |
| 3) | female | 61 | 31 | 30 | 5 |
| 4) | female | 49 | 20 | 29 | 5 |
| 5) | male | 64 | 53 | 11 | 5 |
| 6) | male | 76 | 53 | 23 | 6 |
| 7) | female | 63 | 48 | 15 | 4 |
| 8) | female | 67 | 64 | 3 | 3 |
| 9) | female | 77 | 60 | 17 | 5 |
| 10) | female | 62 | 50 | 12 | 4 |
| 11) | female | 73 | 21 | 52 | 10 |
| 12) | female | 63 | 44 | 19 | 4 |

In Table 1, the motility dysfunction level was scored as 0: No abnormality in walking or running; 1: Slow running speed; 2: Abnormality in walking (stumbling, stiffness of knees); 3: Unable to canter; 4: Handrail needed for ascending or descending stairs; 5: Walking while holding on to something with one hand; 6: Unable to walk while holding on to something with one hand, but able to walk 10 m or more with both hands; 7: Able to walk 5 m or more but not more than 10 m while holding on to something with both hands; 8: Able to walk not more than 5 m while holding on to something with both hands; 9: Unable to walk while holding on to something with both hands, but able to move on all fours; 10: Unable to move on all fours, but able to move with knees, hip or the like on the floor; 11: Unable to move by oneself, but able to roll over; 12: Unable to roll over; and 13: Unable to move even a toe (see Osame M. et al., HTLV-I-associated myelopathy (HAM) revisited. HTLV-I and the Nervous System, Alan R. Liss, Inc, p. 213-223, 1989).

[Results]

Figure 1:
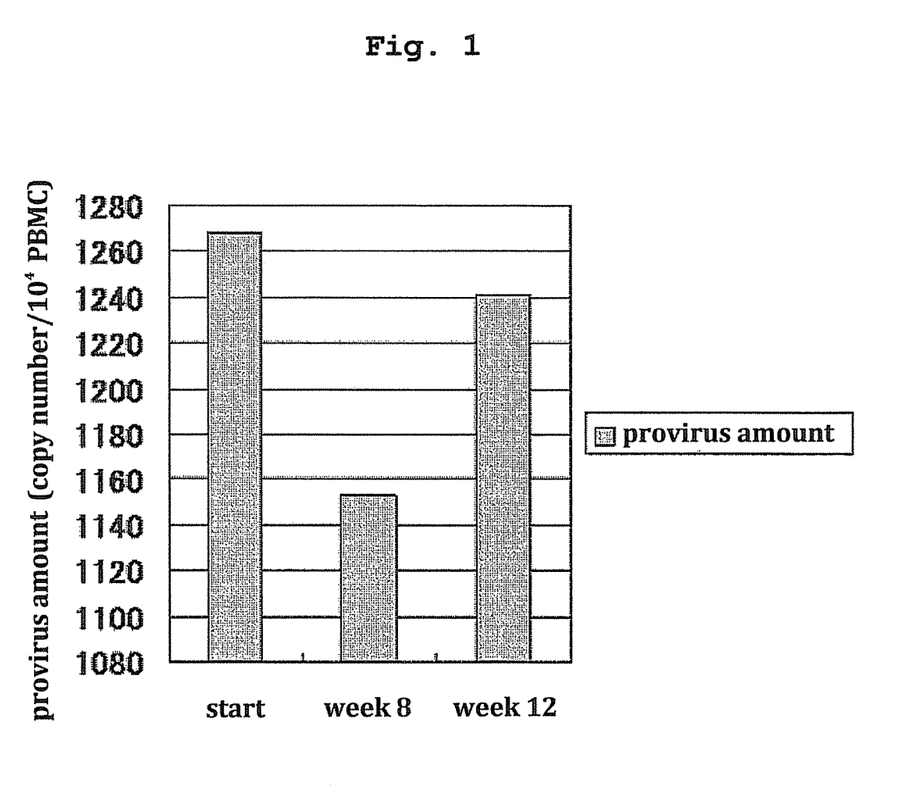
FIG. 1 is a graph showing the average values of the amount of HTLV-I provirus in the test subject before a treatment with pentosan polysulfate, and 8 weeks and 12 weeks after the start of the treatment.

A significant difference was not observed in the lymphoblastogenesis test (Table 2), the soluble IL-2 receptor (sIL-2R) test (Table 3), and the anti-HTLV-I antibody test (Table 4). As for the amount of HTLV-I provirus, no significant difference was found in all 12 cases on week 8 from the start of the treatment, but an average of about 9% decrease was found, and a tendency of returning to the amount at the start of the treatment was found on week 5 after the completion of administration (week 12) (Table 5, FIG. 1).

TABLE 2 lymphoblastogenesis test (stimulation index to PHA)

| | start | week 8 | week 12 |
|---|---|---|---|
| 1) | 8.8 | 9.4 | 9.3 |
| 2) | 3.6 | 3.7 | 4.9 |
| 3) | 7.4 | 9.7 | 9.2 |
| 4) | 9.7 | 11.9 | 12.2 |
| 5) | 6.5 | 8.2 | 6.9 |
| 6) | 10.3 | 9.2 | 6.1 |
| 7) | 11.1 | 12.4 | 7.1 |
| 8) | 5.3 | 4.7 | 6.7 |
| 9) | 12.3 | 7.9 | 15 |
| 10) | 14 | 16.3 | 18.1 |
| 11) | 17.6 | 14 | 24.7 |
| 12) | 18.3 | 13.3 | 17.2 |

TABLE 3 sIL-2R (pg/ml)

| | start | week 2 | week 8 | week 12 |
|---|---|---|---|---|
| 1) | 1512 | 1405 | 1954 | 1864 |
| 2) | 2052 | 2264 | 2420 | 2516 |
| 3) | 1440 | 1256 | 1452 | 1480 |
| 4) | 1944 | 1688 | 1774 | 1882 |
| 5) | 1626 | 1474 | 1964 | 1774 |
| 6) | 557 | 511 | 577 | 627 |
| 7) | 1535 | 1462 | 1482 | 1357 |
| 8) | 898 | 1086 | 904 | 914 |
| 9) | 810 | 933 | 1152 | 1073 |
| 10) | 1504 | 1475 | 1475 | 1557 |
| 11) | 1574 | 1741 | 1551 | 1706 |
| 12) | 1552 | 1524 | 1460 | 1716 |

TABLE 4 anti-HTLV-I antibody (PA method)

| | start | week 8 | week 12 |
|---|---|---|---|
| 1) | $2^{13}$ | $2^{14}$ | $2^{14}$ |
| 2) | $2^{15}$ | $2^{16}$ | $2^{16}$ |
| 3) | $2^{12}$ | $2^{12}$ | $2^{13}$ |
| 4) | $2^{15}$ | $2^{15}$ | $2^{15}$ |

TABLE 4-continued anti-HTLV-I antibody
(PA method)

| | start | week 8 | week 12 |
|---|---|---|---|
| 5) | $2^{13}$ | $2^{13}$ | $2^{13}$ |
| 6) | $2^{11}$ | $2^{11}$ | $2^{11}$ |
| 7) | $2^{13}$ | $2^{14}$ | $2^{14}$ |
| 8) | $2^{11}$ | $2^{10}$ | $2^{11}$ |
| 9) | $2^{13}$ | $2^{13}$ | $2^{13}$ |
| 10) | $2^{13}$ | $2^{13}$ | $2^{12}$ |
| 11) | $2^{13}$ | $2^{13}$ | $2^{14}$ |
| 12) | $2^{13}$ | $2^{13}$ | $2^{13}$ |

TABLE 5

HTLV-I provirus amount (copy number/$10^4$ PBMC)

| | start | week 8 | week 12 |
|---|---|---|---|
| 1) | 2180 | 2030 | 2380 |
| 2) | 1915 | 1621 | 1971 |
| 3) | 846 | 837 | 853 |
| 4) | 1911 | 1900 | 1794 |
| 5) | 2051 | 1140 | 1750 |
| 6) | 709 | 648 | 668 |
| 7) | 920 | 699 | 697 |
| 8) | 582 | 503 | 471 |
| 9) | 1019 | 999 | 1032 |
| 10) | 1809 | 2149 | 2052 |
| 11) | 463 | 479 | 460 |
| 12) | 807 | 830 | 767 |
| average | 1268 | 1153 | 1241 |

Figure 2:
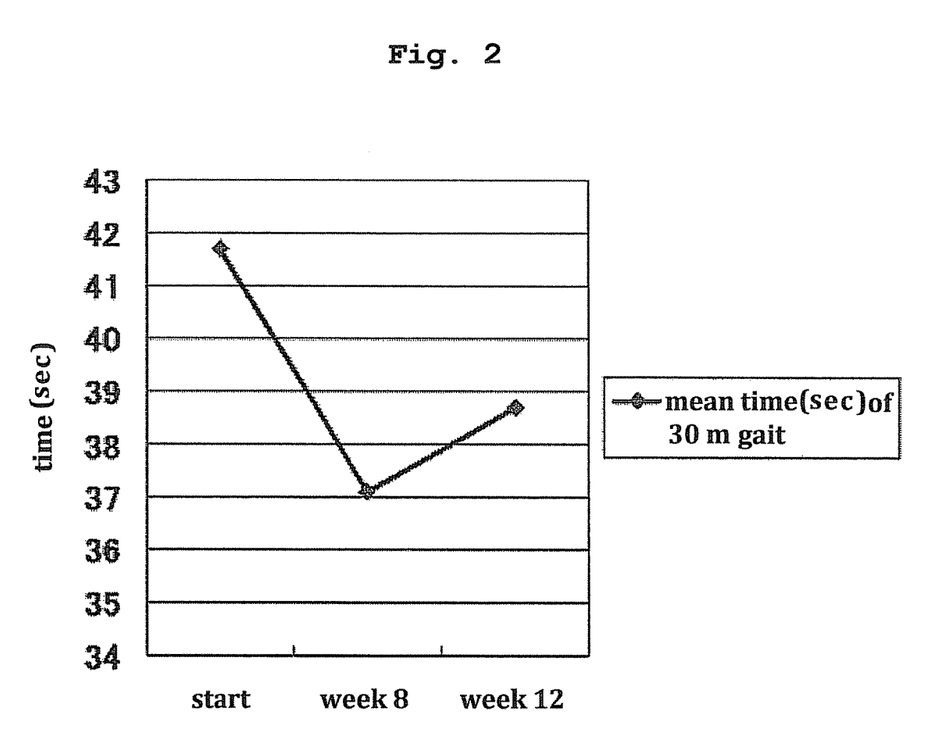
FIG. 2 is a graph showing the average values of a 30 m walking time of the test subject before a treatment with pentosan polysulfate, and 8 weeks and 12 weeks after the start of the treatment.
Figure 3:
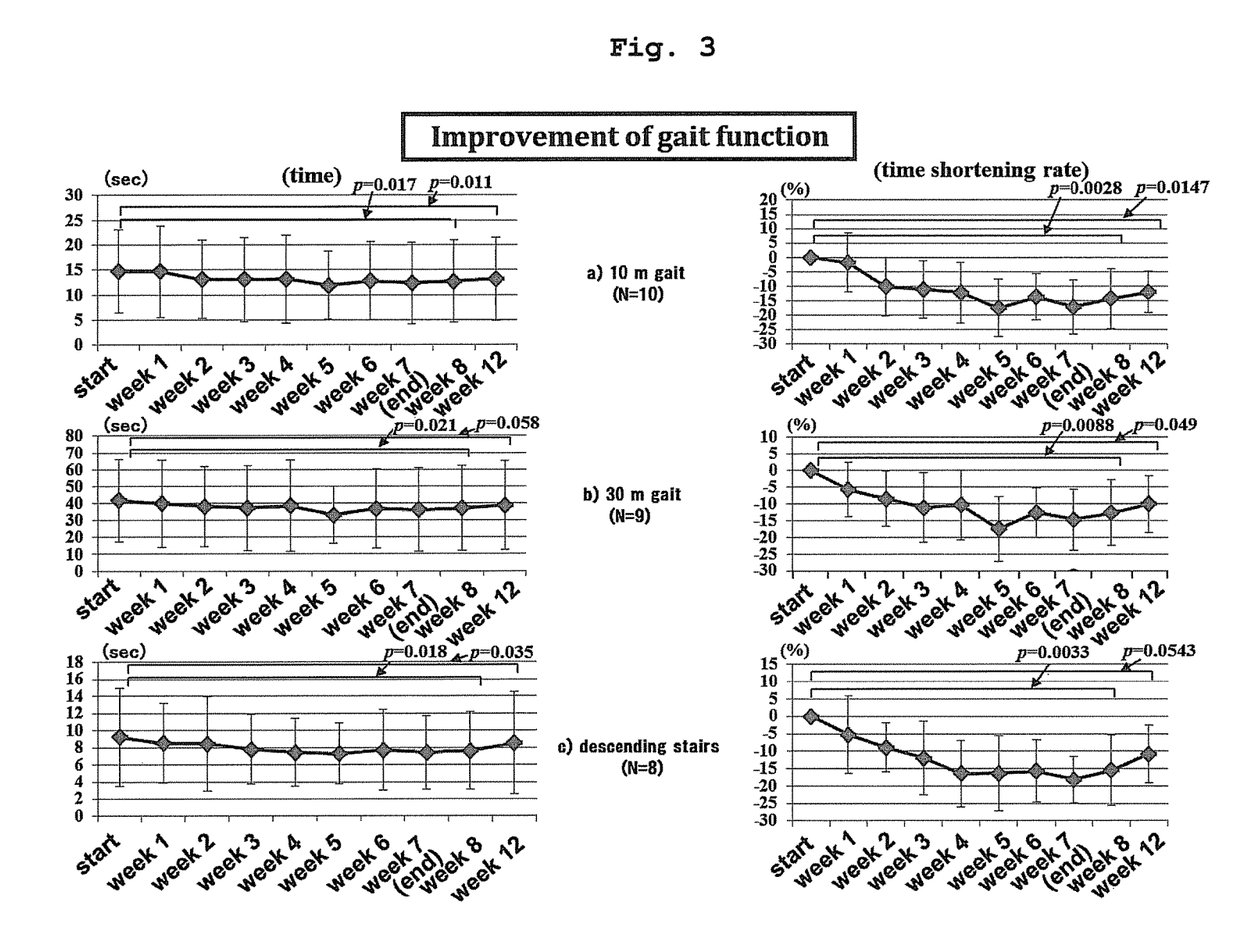
FIG. 3 shows the results of 10 m gait (a), 30 m gait (b), and descending stairs (c) at the start of the treatment with pentosan polysulfate, week 1, week 2, week 3, week 4, week 5, week 6, week 7 (completion of treatment), week 8, and week 12 from the start, as average values of the tested cases. In each of a), b), c), the left shows a required time and the right shows a time shortening rate.

On the other hand, an improvement in the aforementioned motility dysfunction level was found only in one case (from 6 to 5 in week 8), and changes were not found in other cases. However, as to the 10 m gait (Table 6), 30 m gait (Table 7) and descending stairs (Table 8), the time was shortened in almost all cases, and improvement was also confirmed in the mean value of the cases tested for these items (Table 9, FIG. 2 and FIG. 3). Particularly notable as characteristics of the effects on the gait disorder was that improvement was found from considerably early stages after the start of the treatment even in patients suffering from the disease for a long time (24.1 years on average) and having severe motility dysfunction. In addition, improvement of spasticity was also found (Table 10). The improvement of the gait function is considered to be caused by the improvement of spasticity which forms the basis of spastic paraplegia. An adverse event by the administration of pentosan polysulfate was not found in any cases.

TABLE 6

10 m gait (seconds)

| | start | week 8 | week 12 |
|---|---|---|---|
| 1) | 14.5 | 11.5 | 12.5 |
| 3) | 8.1 | 6.5 | 6.5 |
| 4) | 31.3 | 32.5 | 31.9 |
| 5) | 17 | 13.9 | 15.8 |
| 6) | 24.1 | 18.5 | 19.9 |
| 7) | 8 | 7.5 | 7.1 |
| 8) | 5.9 | 5.5 | 5.3 |
| 9) | 19.1 | 15.8 | 16.9 |
| 10) | 6.7 | 6.4 | 6.2 |
| 12) | 12.6 | 8.9 | 9.7 |

(significant difference between start and week 8 and week 12)

TABLE 7

30 m gait (seconds)

| | start | week 8 | week 12 |
|---|---|---|---|
| 1) | 41.8 | 36.5 | 38.1 |
| 3) | 25.3 | 20.5 | 20.5 |
| 4) | 92.7 | 96.5 | 97.5 |
| 5) | 46.9 | 41.6 | 45.4 |
| 6) | | | |
| 7) | 26 | 22.1 | 22 |
| 8) | 17.9 | 16.8 | 16.6 |
| 9) | 65.9 | 52.3 | 59.6 |
| 10) | 21.7 | 20.8 | 19.8 |
| 12) | 37.5 | 26.7 | 28.6 |

(significant difference between start and week 8 and week 12)

TABLE 8 descending stairs (10 stairs) (seconds)

| | start | week 8 | week 12 |
|---|---|---|---|
| 1) | 8.8 | 7.4 | 8.7 |
| 3) | 5.1 | 4.1 | 4 |
| 4) | | | |
| 5) | 10.5 | 9.1 | 8.9 |
| 6) | | | |
| 7) | 5.8 | 4.8 | 4.9 |
| 8) | 4.3 | 4 | 4 |
| 9) | 20.7 | 17.5 | 21.2 |
| 10) | 4.8 | 4.8 | 4 |
| 12) | 14 | 9.1 | 12.4 |

(significant difference between start and week 8 and week 12)

TABLE 9 mean value

| | at start | week 8 | week 12 |
|---|---|---|---|
| 10 m | 14.7 | 12.7 | 13.2 |
| 30 m | 41.7 | 37.1 | 38.7 |
| descending stairs | 9.3 | 7.6 | 8.5 |

TABLE 10 improvement of spasticity (evaluated on modified Ashworth scale (MAS))
(evaluated (+) when either lower leg improved by 1 grade or more) (blank means absent from the start)

| | |
|---|---|
| 1) | (+) |
| 2) | (−) |
| 3) | (+) |
| 4) | (+) |
| 5) | (+) |
| 6) | (+) |
| 7) | (+) |
| 8) | |
| 9) | (+) |
| 10) | |
| 11) | |
| 12) | (+) |

From the above, it was found that pentosan polysulfate can, in addition to the effect of decreasing the provirus amount in HAM patients, achieve improvement of lower leg movement disorder due to spastic paraplegia based on the spasticity of lower leg, which is a pathology of HAM. These results suggest a possibility of pentosan polysulfate as a radical treatment of HAM.

INDUSTRIAL APPLICABILITY

Since the medicament of the present invention can decrease HTLV-I infected cells at the end of the life of the infected cells by preventing spread of HTLV-I in the body of a subject, it can be a causal therapy of HAM. Apart from the effect of decreasing HTLV-I infected cells, it can improve or prevent progression of the clinical symptoms of HAM, particularly lower leg movement disorder. Various medicaments used heretofore for the treatment of HAM failed to show an improvement effect based on the medicinal action unlike the compound used in the present invention, and therefore, the compound can be the first medicament that can improve or prevent progression of the clinical symptoms of HAM. Since the medicament of the present invention expresses the effect at a low dose, it is highly safe and provides effects at a low administration frequency such as once a week and the like. Therefore, the medicament places only a small burden on HAM patients, is superior in the improvement of QOL, and can reduce an economical burden on patients. Furthermore, since pentosan polysulfate is already commercially available as a pharmaceutical product for other applications, the medicament of the present invention can be expected for early practicalization.

This application is based on a patent application No. 2011-226209 filed in Japan (filing date: Oct. 13, 2011), the contents of which are incorporated in full herein.

The invention claimed is:

1. A method of improving a movement disorder of a lower leg resulting from HTLV-I-associated myelopathy (HAM), which comprises administering to a mammal with a movement disorder of a lower leg resulting from HAM pentosan polysulfate or a pharmaceutically acceptable salt thereof as an active ingredient at a dose of about 25 mg to about 150 mg at an administration interval of once in 2 to 7 days, thereby improving the movement disorder of a lower leg resulting from HAM in the mammal, wherein the movement disorder is spasticity or a gait disorder due to spastic paraplegia.

2. The method according to claim 1, wherein the movement disorder is a gait disorder due to spastic paraplegia.

3. The method according to claim 2, wherein the active ingredient is administered at a dose of about 50 mg to about 100 mg at an administration interval of once in 3 to 7 days.

4. The method according to claim 2, wherein the active ingredient is parenterally administered.

5. The method according to claim 4, wherein the active ingredient is parenterally administered via injection.

6. The method according to claim 2, wherein sodium pentosan polysulfate is subcutaneously administered at a dose of 25 mg for the first administration, about 50 mg one week after the first administration, and about 100 mg once a week from the second week to the seventh week.

7. The method according to claim 1, wherein the active ingredient is administered at a dose of about 50 mg to about 100 mg at an administration interval of once in 3 to 7 days.

8. The method according to claim 1, wherein the active ingredient is parenterally administered.

9. The method according to claim 8, wherein the active ingredient is parenterally administered via injection.

10. The method according to claim 1, wherein sodium pentosan polysulfate is subcutaneously administered at a dose of 25 mg for the first administration, about 50 mg one week after the first administration, and about 100 mg once a week from the second week to the seventh week.

* * * * *

UNITED STATES PATENT AND TRADEMARK OFFICE
CERTIFICATE OF CORRECTION

| | | |
|---|---|---|
| PATENT NO. | : 9,763,973 B2 | Page 1 of 1 |
| APPLICATION NO. | : 14/351242 | |
| DATED | : September 19, 2017 | |
| INVENTOR(S) | : Nagasaki et al. | |

It is certified that error appears in the above-identified patent and that said Letters Patent is hereby corrected as shown below:

On the Title Page

In the abstract: Line 1, delete the word "or"

In the Claims

Claim 6 at Column 18, Line 18, "dose of 25 mg" should read "dose of about 25 mg"

Claim 10 at Column 18, Line 30, "dose of 25 mg" should read "dose of about 25 mg"

Signed and Sealed this
Second Day of January, 2018

Joseph Matal
*Performing the Functions and Duties of the*
*Under Secretary of Commerce for Intellectual Property and*
*Director of the United States Patent and Trademark Office*